(12) United States Patent
Kuenzi et al.

(10) Patent No.: US 8,500,745 B2
(45) Date of Patent: Aug. 6, 2013

(54) AIMING DEVICE FOR INSERTING STABLE-ANGLE, LONG SCREWS IN THE ARTICULAR REGION OF A BONE

(75) Inventors: Thomas Kuenzi, Birsfelden (CH); Daniel Andermatt, Mohlin (CH); Gregor Feigenwinter, Basel (CH)

(73) Assignee: Depuy Synthes Products, LLC, Raynham, MA (US)

( * ) Notice: Subject to any disclaimer, the term of this patent is extended or adjusted under 35 U.S.C. 154(b) by 1407 days.

(21) Appl. No.: 10/590,044

(22) PCT Filed: Feb. 20, 2004

(86) PCT No.: PCT/IB2004/000441
§ 371 (c)(1),
(2), (4) Date: May 2, 2007

(87) PCT Pub. No.: WO2005/089660
PCT Pub. Date: Sep. 29, 2005

(65) Prior Publication Data
US 2007/0239168 A1    Oct. 11, 2007

(51) Int. Cl.
*A61B 17/17* (2006.01)
(52) U.S. Cl.
USPC .......................................... 606/96; 606/86 R
(58) Field of Classification Search
USPC .................. 269/143, 249; 606/86 R, 88–89, 606/96, 98–99, 104, 151, 280–282; 623/18.11, 623/19.13–19.14, 20.11, 20.14, 20.21
See application file for complete search history.

(56) References Cited

U.S. PATENT DOCUMENTS

| 3,674,375 | A | * | 7/1972 | Reed et al. | 408/103 |
| 3,867,932 | A | * | 2/1975 | Huene | 606/80 |
| 4,159,716 | A | * | 7/1979 | Borchers | 606/96 |
| 4,235,428 | A | * | 11/1980 | Davis | 606/96 |
| 4,364,381 | A | * | 12/1982 | Sher et al. | 606/96 |
| 4,465,065 | A | * | 8/1984 | Gotfried | 606/65 |

(Continued)

FOREIGN PATENT DOCUMENTS

| EP | 0 132 284 A | | 1/1985 |
| EP | 132284 A1 | * | 1/1985 |
| EP | 1 354 562 A | | 10/2003 |
| WO | WO 03/041595 A1 | | 5/2003 |

OTHER PUBLICATIONS

International Search Report of PCT/IB2004/000441, mail date Nov. 11, 2004.

*Primary Examiner* — Nicholas Woodall
*Assistant Examiner* — Larry E Waggle, Jr.
(74) *Attorney, Agent, or Firm* — Fay Kaplun & Marcin, LLP

(57) ABSTRACT

The invention relates to an aiming device (100) for boring a hole in a region of a bone (300) that lies in the vicinity of a joint. Said device consists of a U-shaped bow (110) comprising at least one contact element (120) on one end and on the other end of the bow (110) a screw spindle (130) that can be displaced in the direction of, or in the opposite direction to the contact element (120), said spindle comprising a rotary grip (132) for clamping the device (100) on the region in the vicinity of the joint. The device also comprises a bore bushing (140), which can be placed on and removed from the end comprising the contact element (120). The compression of the bone that is generated by the bow (110) is maintained after the removal of the bore bushing (140) for the insertion of the bone screw.

15 Claims, 5 Drawing Sheets

U.S. PATENT DOCUMENTS

Figure 1:
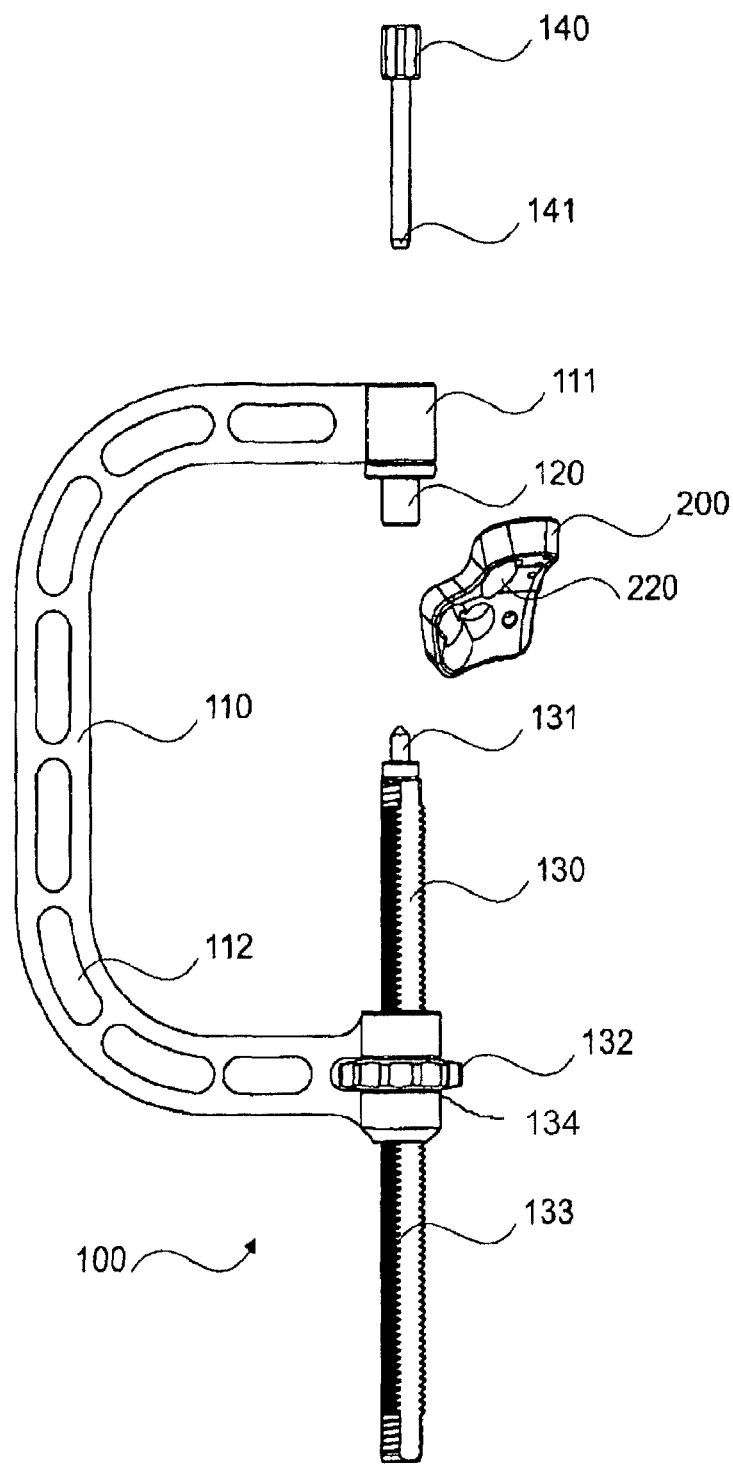

| | | | |
|---|---|---|---|
| 4,625,718 A | 12/1986 | Olerud et al. | |
| 4,710,075 A * | 12/1987 | Davison | 408/202 |
| 4,848,327 A | 7/1989 | Perdue | |
| 4,997,434 A * | 3/1991 | Seedhom et al. | 606/80 |
| 5,152,764 A * | 10/1992 | Goble | 606/96 |
| 5,254,079 A * | 10/1993 | Agbodoe et al. | 602/32 |
| 5,409,493 A | 4/1995 | Greenberg | |
| 5,713,117 A * | 2/1998 | Bliss | 29/257 |
| 5,893,553 A * | 4/1999 | Pinkous | 269/249 |
| 6,299,616 B1 * | 10/2001 | Beger | 606/86 R |
| 2002/0032465 A1 | 3/2002 | Lemer | |
| 2002/0087163 A1 * | 7/2002 | Dixon et al. | 606/90 |
| 2003/0009171 A1 | 1/2003 | Tornier | |
| 2003/0220651 A1 | 11/2003 | Pusnik et al. | |
| 2004/0102788 A1 * | 5/2004 | Huebner et al. | 606/96 |

* cited by examiner

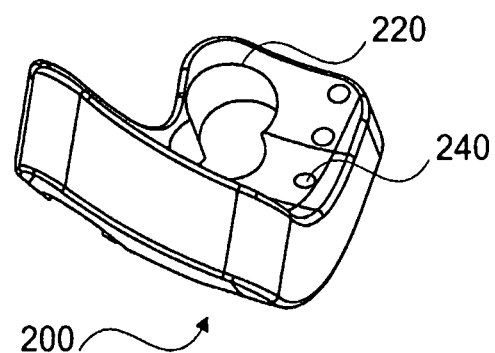
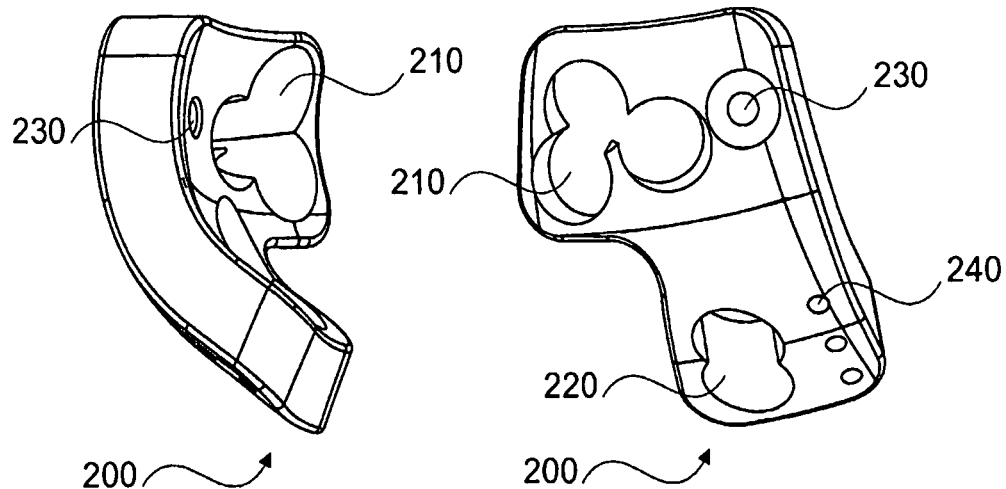
Fig.3
Fig.4
Fig.5

AIMING DEVICE FOR INSERTING STABLE-ANGLE, LONG SCREWS IN THE ARTICULAR REGION OF A BONE

The invention relates to an aiming device for inserting angle-stable, long screws in the articular region of a bone for optimal treatment of joint fractures with plate/screw systems, using a distal humerus as an example.

For example, the patents US-20020032465-A1, US-20030220651-A1, U.S. Pat. No. 4,625,718, U.S. Pat. No. 4,848,327 and WO-03041595-A1 may be mentioned in relation to the prior art.

However, US 2003/0009171 A1 will be discussed in particular. This discloses a multiplicity of aids for fitting an elbow prosthesis, in particular an aiming device for drilling the articular region of the bone along its joint axis. This aiming device consists of a bow which is clamped on the articular region by means of a screw spindle. A guide zone for inserting a drill into the articular region along said joint axis is integrated in the screw spindle. The bore which can be produced in this manner serves here for inserting a pin which subsequently permits alignment of the elbow prosthesis and is then removed again. The insertion of a screw is not envisaged in this apparatus.

Even if this device disclosed in US 2003/0009171 A1 is intended for a completely different purpose, the preparation of bores therewith which is intended by the inventor could in certain circumstances be carried out, even if with considerable disadvantages. The known device has no possibility for preventing the risk of penetration into the joint, which is also unimportant in the course of fitting an elbow prosthesis since the joint is removed in any case and is replaced. However, during osteosynthesis, treatment of the bone in as gentle a manner as possible is a precondition. As already mentioned, the placing of the distal screw required in osteosynthesis after drilling is complete is possible only if the device or at least the screw spindle were to be removed. However, this would eliminate the compression produced by the device for ensuring cohesion of any bone fragments. During the entire course of the operation with this known device, continuous stability is therefore not possible. Finally, the drill would disadvantageously have to have at least the length of the screw spindle and of the desired drilled hole, with the result that increased vibrations may adversely influence the drilling.

It is the object of the present invention to eliminate these disadvantages.

It should be possible by means of the invention to insert distal screws which are as long as possible through the bone in that region of the articular block which is in the vicinity of the joint, for which purpose the bores are accordingly to be introduced in a targeted manner and without any penetration into the joint, with the result that, after insertion of a screw, optimal fixation in the good bone should be achieved. Any screws opposite to one another should moreover be capable of being brought past one another as closely as possible in a targeted manner and approximately along an axis without collision. This should be ensured in particular directly during the first attempt in order to protect the bone as far as possible. The compression of the bone fragments of the articular block during the entire duration of the operation is also to be maintained in order thereby to ensure a stable connection and good clinical results.

The aiming device according to the invention and according to claim 1 consists of a bow, optionally having various cut-outs for weight reduction, and achieves the objects set. A preferred embodiment has the following design, a screw spindle which can be actuated by means of a nut and is intended for fixing the aiming device on the articular region of the bone is provided on the bow. A cylindrical guide which in turn bears an adaptor bush so as to permit rotational movement is mounted on the opposite end of the bow. Cylindrical guide and adaptor bushing are suitable firstly for guiding a bone screw and secondly for bearing a drill bushing having preferably an external thread. A target plate for connection to a bone plate is intended for producing a temporary plug connection with the adaptor bushing of the aiming device.

Course of the Operation

Before the operation, the target plate is screwed to a lateral implant (bone plate). By means of the plug connection, the target plate with the lateral implant is mounted on the adaptor bushing of the aiming device. The drill bushing is then inserted into the orifice in the cylindrical guide and, passing through the adaptor bushing and the target plate; comes into contact with complementary internal thread in a bore of the implant. Everything is now placed together on the fragmented bone, clamped by the screw spindle of the aiming device and fixed with a proximal bone screw through the implant. With the aid of the aiming device according to the invention, it is therefore possible to determine the point of emergence of the distal, angle-stable screws prior to drilling. When everything is correctly aligned, drilling can be effected through the integrated drill bushing. Furthermore, the length of the screw to be used and hence the depth of the hole to be drilled can be determined directly using the aiming device, in particular with reference to the scale mounted on its screw spindle.

After removal of the drill bushing screwed to the implant, the compression persists via the plug connection between adaptor bushing and target plate. This is an important advantage in contrast to the known device. By using the target plate, it is therefore possible, after removal of the drill bushing, to screw in the screw while the aiming bow is mounted, i.e. under compression. The removed drill bushing now also frees the larger diameter required by the bone screw. The bone screw fits firmly with its head on the same implant thread which the drill bushing has previously held. In addition, the alignment of further screws is simplified in that the position of the already inserted screw is indicated by the aiming device so that they are inserted in a completely targeted manner parallel to the joint axis and through the best bone of the distal part. When this has been completed, the aiming device and the target plate can be removed.

Further developments of the invention are shown in the Figures and indicated in the independent patent claims.

The list of reference numerals is part of the disclosure.

The invention is explained in more detail schematically and by way of example with reference to figures.

The figures are described in relation to one another and as a whole. Identical reference numerals denote identical components, and reference numerals with different indices indicate functionally identical or similar components.

Figure 2:
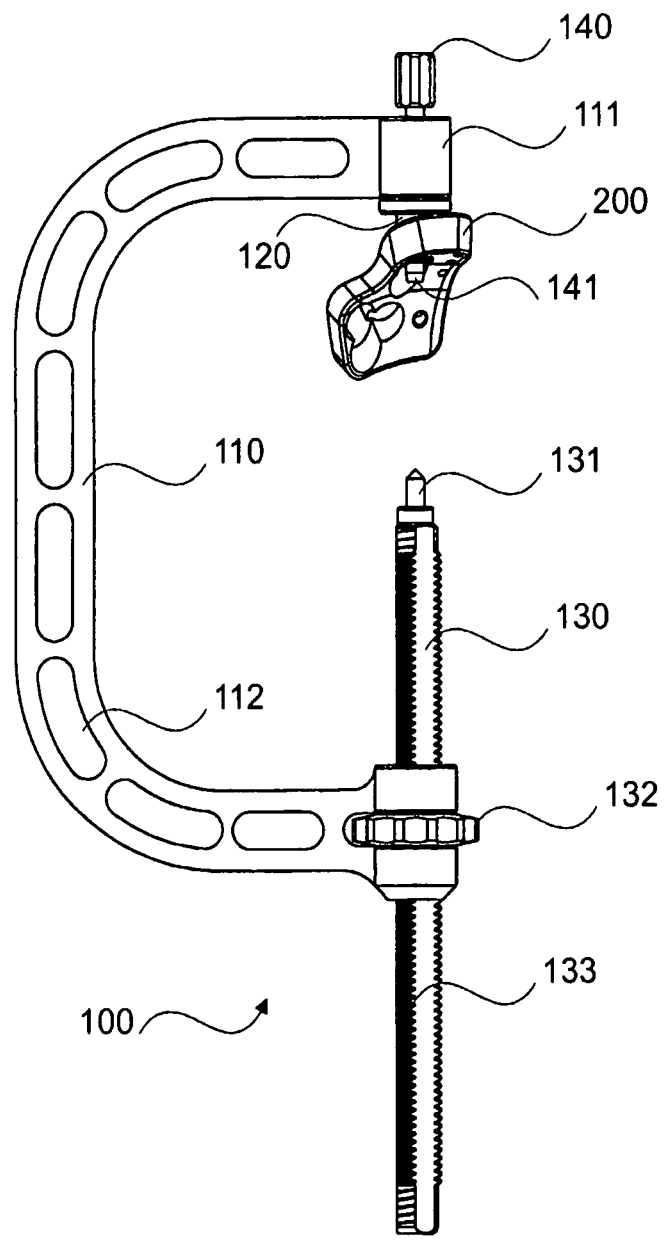
Figure 6:
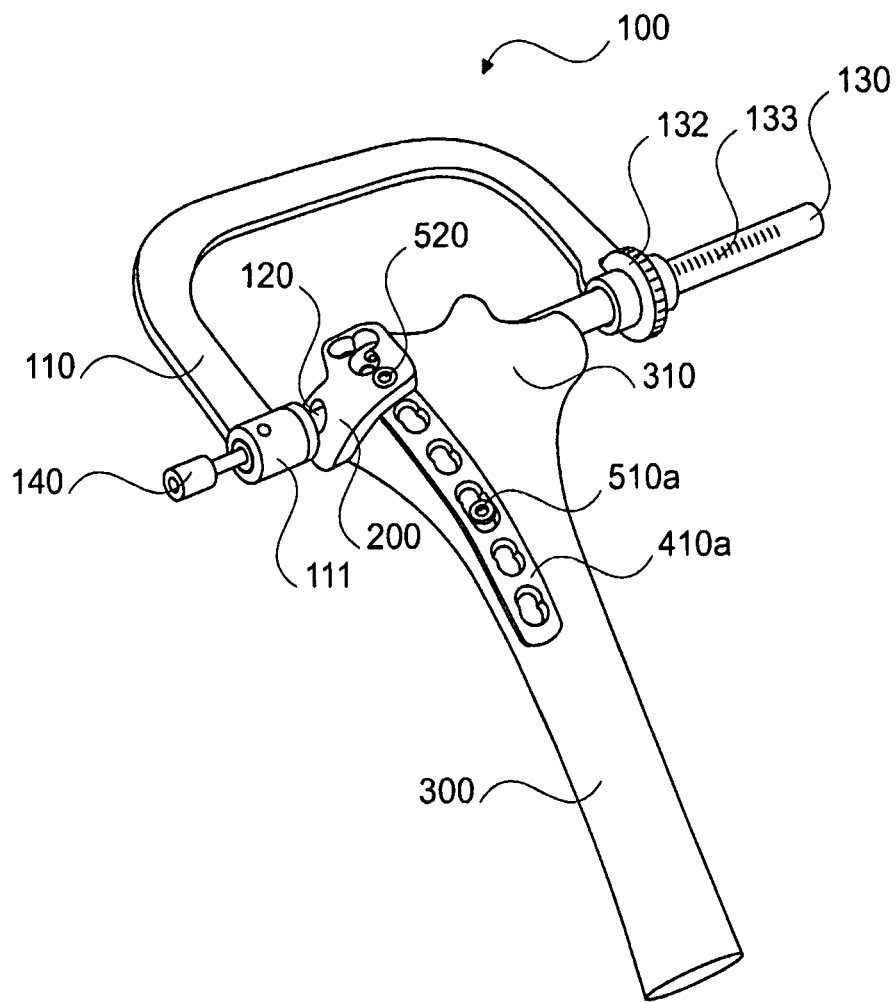
Figure 7:
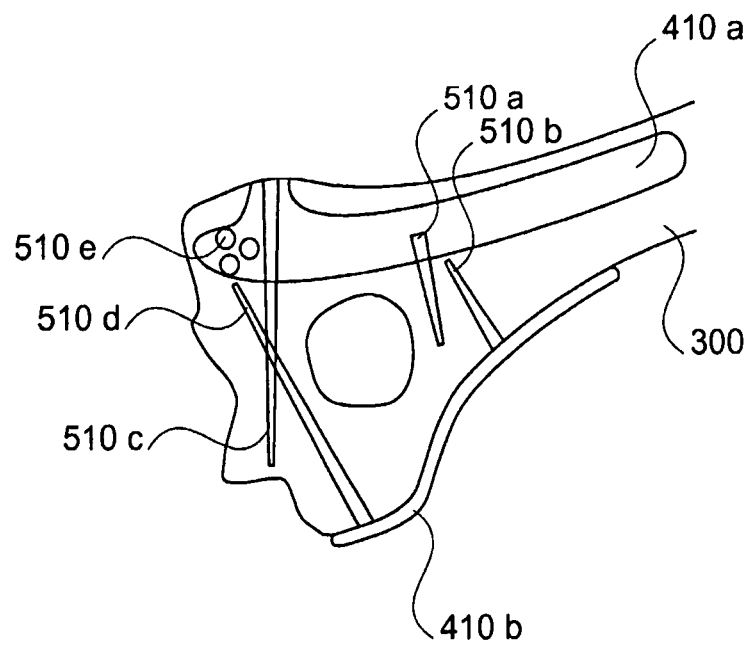

FIG. 1 shows an aiming device according to the invention, having a separate drill bushing and target plate, in the frontal view, FIG. 2 shows the aiming device according to FIG. 1 with mounted drill bushing and target plate, in frontal view, FIG. 3 to 5 show the target plate according to FIGS. 1 and 2 alone, in three different views, FIG. 6 shows a schematic diagram of the aiming device with mounted drill bushing, target plate and implant screwed thereto, as mounted on the humerus, in perspective view, and FIG. 7 shows a schematic diagram of the humerus with implants and bone screws in the frontal plane.

FIG. 1 shows an aiming device 100 having a separate drill bush 140 and target plate 200. The target plate 100 consists of a U-shaped bow 110 having various cut-outs 112. A screw spindle 130 adjustable by means of a nut 132 is mounted in a recess 134 extending through the lower end of the bow 110. A rotationally movable pin 131 is arranged on one end of the screw spindle 130. A scale 133 is mounted on the screw spindle 130. A cylindrical guide 111 which in turn bears an adaptor bush 120 in a rotationally movable manner is arranged on the upper end of the bow 110. Cylindrical guide 111 and adaptor bush 120 have an internal diameter which is suitable firstly for guiding a bone screw (not shown) and secondly for bearing a drill bush 140. This drill bush 140 is equipped at its end with a drill bush thread 141 which, when an implant (not shown) is used, engages said implant. The adaptor bush 120 is equipped with a snap element which finds its counterpart in a bore 220 of a target plate 200. The target plate 200 is therefore intended for producing a temporary plug connection to the aiming device 100, as shown in FIG. 2.

FIG. 2 shows the aiming device 100 with mounted drill bushing 140 and target plate 200. The target plate 200 has a plug connection to the adaptor bushing 120 described in FIG. 1. The drill bushing 140 is inserted into the orifice in the cylindrical guide 111 and, on passing through the adaptor bushing and the target plate 200 appears with its drill bushing thread 141.

FIG. 3 to 5 show the target plate 200 in three different views. Said target plate has a bore 220 for the adaptor bushing (not shown) which can thereby produce a plug connection to the target plate 200. Furthermore, three bores 210 for anterior-posterior bone screws are formed, one bore 230 for a target plate screw and three bores 240 for Kirschner wires.

FIG. 6 shows a schematic diagram of the aiming device 100 with mounted drill bushing 140, target plate 200 and lateral implant 410a screwed thereto, as mounted on the articular block 310 of the humerus 300. The instrument set is therefore mounted as described in FIG. 2, the lateral implant 410a additionally being screwed on the one hand by means of a target plate screw 520 through the bore 230 shown in FIG. 3 to 5 and intended for the target plate screw (not visible) to the target plate 200. On the other hand, a thread (not shown) of the lateral implant 410a engages the drill bushing 140, in particular its drill bushing thread 141, which passes through the adaptor bushing 120. The entire structure is clamped on the articular block 310 of the humerus 300 by the screw spindle 130 actuatable by means of the nut 132 and is anchored in the humerus 300 by means of a proximal bone screw 510a through the implant 410a.

FIG. 7 shows a schematic diagram of the humerus with implants and bone screws in the frontal plane. The lateral implant 410a is fixed by means of proximal 510a, distal 510c and anterior-posterior 510e bone screws. The medial implant 410b is fixed by means of proximal 510b and distal 510d bone screws. In particular, the bone screws 510c and 510d are chosen to be as long as possible without penetrating into the joint and are guided past one another as closely as possible.

LIST OF REFERENCE NUMERALS

100—Aiming device
110—Bow
111—Cylindrical guide
112—Cut-out
120—Adaptor bushing or contact element
130—Screw spindle
131—Pin
132—Nut or rotary grip
133—Scale
140—Drill bushing
141—Drill bushing thread
200—Target plate
210—Bore for anterior-posterior bone screw
220—Bore for adaptor bushing
230—Bore for target plate screw
240—Bore for Kirschner wire
300—Bone (humerus)
310—Articular block (of the humerus)
410—Implant
410a—Lateral implant
410b—Medial implant
510—Bone screw
510a—Proximal bone screw (lateral)
510b—Proximal bone screw (medial)
510c—Distal bone screw (lateral)
510d—Distal bone screw (medial)
510e—Anterior-posterior bone screw
520—Target plate screw

The invention claimed is:

1. An aiming device for drilling a hole in a region of a bone which is in the vicinity of a joint, comprising: a U-shaped bow having at least one contact element at a first end of the bow and, at a second end of the bow a screw spindle movable towards and away from the contact element and having a rotary grip, for clamping the device to the region of the bone in the vicinity of the joint, and a drill bushing, wherein the drill bushing can be removably inserted through the contact element, the drill bushing being configured to guide insertion of an instrument therethrough and into a portion of bone in contact with the contact element, a bone compression produced by the bow persisting after removal of the drill bushing for insertion of a bone screw.

2. The aiming device according to claim 1, wherein the bone screw is configured for insertion between the contact element and a target bone plate.

3. The device according to claim 1, wherein the contact element is a rotationally movable adaptor bushing.

4. The device according to claim 3, wherein the adaptor bushing can be caused to form a plug connection with a target plate which can be screwed onto an implant.

5. The device according to claim 4, wherein the drill bushing can be guided through the adaptor bushing and can be caused to engage the implant.

6. The device according to claim 5, wherein a scale for determining the length of a bone screw to be inserted into the hole is mounted on the screw spindle or on an element firmly connected to or engaging said screw spindle.

7. The device according to claim 6, wherein an end of the screw spindle which faces the contact element has a rotationally movably mounted changeable pin.

8. The device according to claim 1, wherein the rotary grip is in the form of a nut mounted on the screw spindle.

9. The device according to claim 8, wherein the nut is mounted in a recess of the bow.

10. The device according to claim 1, wherein the bow is in the form of a lattice structure or has various cut-outs.

11. A method for inserting distal angle-stable, long screws in the articular region of a bone, comprising the steps of: screwing a target plate to a lateral implant prior to performing a target procedure, the target plate and lateral implant being mounted on an adaptor bushing of an aiming device by a plug connection; inserting a drill bushing into an orifice of a cylindrical guide, wherein the drill bushing, on passing through the adaptor bushing and the target plate, comes into contact with a complementary internal thread in a bore of the lateral implant, whereupon the target plate and lateral implant are placed together on a fragmented portion of the bone and clamped by a screw spindle of the aiming device and fixed through the implant by means of a proximal bone screw, so that a point of emergence of the distal, angle-stable long screws can be determined prior to drilling after the target plate and lateral implant have been correctly aligned, drilling can be effected through the integrated drill bushing, it being possible directly to determine the length of the distal angle-stable long screw to be used and hence the depth of the hole to be drilled, in particular on the basis of a scale mounted on the screw spindle; removing the drill bushing; and inserting the distal angle-stable long bone screw while maintaining the compression of the bone.

12. The method according to claim 11, wherein the aiming device comprises a U-shaped bow with a contact element on one end of the bow and the screw spindle on the other end of the bow and the drill bushing removably inserted through the contact element, wherein, when the bow is positioned on the bone, compression is produced by means of the screw spindle against the contact element, a bone bore is then produced while maintaining compression through the drill bushing and the drill bushing is then removed, the compression between screw spindle and contact element persisting, after which the bone screw is screwed into the bone while maintaining the compression.

13. The method according to claim 12, wherein the bow and the contact element are mounted after prior positioning of the lateral implant, so that the lateral implant is kept pressed against the bone by the compression, the lateral implant remaining fixed on the bone by the bone screw.

14. A kit for assembling a device for inserting angle-stable long screws in the articular region of a bone, comprising: a U-shaped bow having a contact element at a first end and an adjustable screw spindle at a second end, a target bone plate which can be connected to the U-shaped bow, a drill bushing capable of being inserted through the contact element, the drill bushing being configured to guide insertion of an instrument therethrough and into a portion of bone in contact with the contact element and an implant which can be temporarily fixed to the target bone plate.

15. The kit of claim 14, wherein the target bone plate is capable of being attached to the implant by a threaded connection with the drill bushing.

* * * * *